(12) United States Patent
Ascione et al.

(10) Patent No.: US 6,632,421 B2
(45) Date of Patent: Oct. 14, 2003

(54) DEODORANT COMPOSITION COMPRISING A WATER-SOLUBLE ZINC SALT AS ODOR-ABSORBING AGENT

(75) Inventors: Jean-Marc Ascione, Paris (FR); Serge Forestier, Claye Souilly (FR); Isabelle Rollat-Corvol, Boulogne (FR)

(73) Assignee: L'Oreal, Paris (FR)

( * ) Notice: Subject to any disclaimer, the term of this patent is extended or adjusted under 35 U.S.C. 154(b) by 79 days.

(21) Appl. No.: 09/846,353

(22) Filed: May 2, 2001

(65) Prior Publication Data

US 2002/0127193 A1 Sep. 12, 2002

Related U.S. Application Data

(63) Continuation of application No. 08/730,061, filed on Oct. 15, 1996.

(51) Int. Cl.$^7$ .............. A61K 7/32; A61K 7/36; A61K 7/00
(52) U.S. Cl. ............. 424/65; 424/67; 424/400; 424/401
(58) Field of Search ............. 424/401, 65, 67

(56) References Cited

U.S. PATENT DOCUMENTS

| | | |
|---|---|---|
| 2,087,161 A | 7/1937 | Moore |
| 4,172,123 A | 10/1979 | Lowicki |
| 4,235,873 A | 11/1980 | Packman |
| 4,425,321 A | 1/1984 | Jacquet et al. |
| 4,565,693 A | 1/1986 | Marschner |
| 4,784,844 A | 11/1988 | Thimineur et al. |
| 4,980,156 A | 12/1990 | Raleigh et al. |
| 4,988,504 A | 1/1991 | Zotto et al. |
| 5,008,103 A | 4/1991 | Raleigh et al. |
| 5,362,494 A | 11/1994 | Zysman et al. |
| 5,456,906 A | 10/1995 | Powell et al. |
| 5,540,853 A | 7/1996 | Trinh et al. |
| 5,643,559 A | 7/1997 | Eigen et al. |
| 5,650,140 A | 7/1997 | Bergmann et al. |
| 5,676,937 A | 10/1997 | Eigen et al. |

FOREIGN PATENT DOCUMENTS

| | | |
|---|---|---|
| EP | 216558 | 4/1987 |
| EP | 330140 | 8/1989 |
| FR | 2398495 | 2/1979 |
| GB | 1536222 | 12/1978 |
| JP | 58 222010 | 12/1983 |
| JP | 3 284617 | 12/1991 |
| JP | 4 036216 | 2/1992 |
| JP | 60 87729 | 3/1994 |
| WO | WO 87/04341 | 7/1987 |
| WO | WO 93/01793 | 2/1993 |

OTHER PUBLICATIONS

Wilkinson et al., Harry's Cosmeticology, pp. Ch4, 743, 1982.

*Primary Examiner*—Shelley A. Dodson
(74) *Attorney, Agent, or Firm*—Finnegan, Henderson, Farabow, Garrett & Dunner, L.L.P.

(57) ABSTRACT

The present invention relates to a deodorant composition, in particular a cosmetic composition, comprising, as odor-absorbing agent, at least one water-soluble zinc salt, and preferably zinc pyrrolidonecarboxylate, to the use of the composition for the manufacture of cosmetic products intended for human topical application, in particular deodorants, to a process for treating human axillary smells, and to the use of a water-soluble zinc salt as, preferably sole, an odor-absorbing agent in a deodorant composition.

The composition is particularly intended for formulations comprising an aqueous phase: aqueous lotions, emulsions and preferably water-in-silicone emulsions.

11 Claims, No Drawings

DEODORANT COMPOSITION COMPRISING A WATER-SOLUBLE ZINC SALT AS ODOR-ABSORBING AGENT

This is a continuation of application Ser. No. 08/730,061 filed, filed Oct. 15, 1996 incorporated herein by reference.

The present invention relates to a deodorant composition comprising at least one water-soluble zinc salt as odour-absorbing agent, in particular a composition comprising the zinc salt as the sole odour-absorbing agent, and to the use of these compositions in human topical application.

It also relates to a deodorization process which makes use of the composition and more especially to a process for treating human axillary smells comprising the application to the axillary surface of an effective amount of the composition.

It is well known in the cosmetics field to use deodorant products in topical application containing active substances of antiperspirant type or of bactericidal type to decrease, indeed remove, the generally unpleasant axillary smells.

Antiperspirant substances have the effect of limiting the flow of sweat. They are generally composed of aluminium salts which, on the one hand, are irritating to the skin and which, on the other hand, decrease the flow of sweat by modifying the cutaneous physiology, which is unsatisfactory.

Bactericidal substances, by inhibiting the development of the cutaneous flora responsible for axillary smells, have the disadvantage of not being active with respect to the smell of the sweat already present. These bactericidal products, the most widely employed of which is triclosan (5-chloro-2-(2, 4-dichlorophenoxy)phenol), are therefore insufficiently effective on a long-term basis.

With the aim of obtaining a longer-lasting effectiveness, the search is under way for deodorant products that exert an odour-absorbing effect, that is to say products that are capable of capturing and retaining within themselves the molecules responsible for unpleasant smells (this definition is given in the work "Cosmetic Science and Technology Series", 1988, Volume 7, Chap. 10-IIIc). These products have the effect of decreasing, to a greater or lesser extent, the smell of sweat already present and do not exhibit the disadvantages of the active substances previously employed in deodorant compositions.

From this viewpoint, certain zinc salts have already been provided. In particular, zinc salts of polycarboxylic acids described in U.S. Pat. No. 4,425,321, which is incorporated herein by reference, and in particular those of dimerginic acid and those of trimerginic acid, which may or may not be hydroxylated, are known.

Nevertheless, such zinc-based odour-absorbers are still not very satisfactory due to the fact that their insolubility in water makes it difficult to formulate them in water-based compositions, which is often the case for formulations intended in particular for a cosmetic use.

After much research directed at this question, the inventors have now discovered, entirely unexpectedly and surprisingly, that water-soluble zinc salts also exhibit the property of absorbing unpleasant smells, without the disadvantages of the active substances previously employed in deodorant compositions and with the advantage of being water-soluble in advantageous proportions that are sufficient for being easily formulable, in particular in water-based cosmetic compositions for human topical application. These compositions are, in addition, non-toxic and non-irritating. This discovery underlies the present invention.

The subject of the present invention is thus a new deodorant composition comprising, as odour-absorbing agent, at least one water-soluble zinc salt.

Another subject of the invention is a deodorant composition comprising, as sole odour-absorbing agent, one or a number of water-soluble zinc salts.

Another subject of the invention is a deodorant composition in the form of an emulsion, comprising at least one water-soluble zinc salt in an amount effective to absorb odor and further comprising water in an amount sufficient to form the emulsion.

Another subject of the invention is a deodorant composition having at least 2 phases and comprising at least one water-soluble zinc salt.

Another subject of the invention is the use of the compositions, more especially in, or for the manufacture of, cosmetic products intended for human topical application.

Another subject of the invention is the use of at least one water-soluble zinc salt as (preferably sole) an odour-absorbing agent, or for the manufacture of, a deodorant composition, in particular a cosmetic composition.

Another subject of the invention is a method of preparing a deodorant composition in the form of an emulsion comprising the step of including in the composition at least one water-soluble zinc salt in an amount effective to absorb odor and water in an amount effective to form an emulsion.

Still another subject of the invention is a deodorization process that makes use of the composition, and more particularly a process for treating human axillary smells, that comprises the application to the axillary surface of an effective amount of the composition.

Within the meaning of the present invention, water-soluble zinc salts is understood to mean zinc salts of organic or inorganic acids, the solubility of which in water, expressed as percentage by weight of Zn ion, is greater than or equal to about 0.3. Water-soluble zinc salts that are particularly preferred according to the present invention are zinc pyrrolidonecarboxylate (more commonly known as zinc pidolate), zinc sulphate, zinc chloride, zinc lactate, zinc gluconate and zinc phenolsulphonate. Among the salts mentioned above, preference is still more particularly given to the use, according to the present invention, of zinc pyrrolidonecarboxylate.

In the deodorant compositions according to the present invention, the water-soluble zinc salt is generally present in proportions by weight, calculated as Zn ion, preferably ranging from approximately 0.01 to approximately 10%, more preferably ranging from approximately 0.1 to approximately 5%, and better still ranging from approximately 0.1 to 2% with respect to the whole of the composition.

According to a preferred embodiment of the compositions according to the invention, the latter do not contain, or do not substantially contain, odour-absorbing agents other than water-soluble zinc salts.

The deodorant compositions of the present invention are conventionally formulated according to the applications for which they are intended. When they are intended for a cosmetic use, they are preferably formulated in a cosmetically acceptable vehicle that can in particular be essentially aqueous and can contain $C_1$–$C_4$ monoalcohols, preferably ethanol, to accelerate evaporation of the product, and/or $C_2$–$C_6$ polyols, preferably glycerol, propylene glycol or sorbitol, as moisturizing agents, in a proportion by weight ranging from 0 to approximately 50%. They can also be formulated as a water-in-oil or oil-in-water emulsion or as a water-in-oil-in-water triple emulsion (such emulsions are known and described, for example, by C. Fox in "Cosmetics and Toiletries", Vol. 101, November 1986, pages 101–112, specifically incorporated by reference herein), in which case the water-soluble zinc salt is present in the aqueous phase of the emulsion. According to a preferred embodiment of the present invention, the compositions are formulated in the form of a water-in-silicone emulsion, which makes it possible according to the invention to reinforce the effectiveness of the water-soluble zinc salt as odour-absorbing agent in comparison with an aqueous formulation containing an equivalent amount of the same water-soluble zinc salt. The water-in-silicone emulsions according to this preferred embodiment comprise: (i) a dispersed aqueous phase and (ii) a continuous silicone fatty phase comprising (a) a volatile dimethicone and (b) a silicone emulsifying agent.

(i) Aqueous Phase

The aqueous phase of these emulsions can contain, in addition to the water-soluble zinc salt as odour-absorbing agent, other ingredients, such as humectants, for example polyols, stabilizers, for example citric acid or lactic acid, and optionally $C_1$–$C_4$ monoalcohols, such as ethanol.

(ii) Continuous Fatty Phase

In the continuous silicone fatty phase of these emulsions, (a) the volatile dimethicone (boiling point less than 250° C.) can be linear or cyclic; it is more preferably chosen from the group formed by fluid methylsiloxanes containing units of formula:

$$(CH_3)_a SiO_{(4-a)/2}$$

in which a represents an approximate value ranging from 2 to 3 inclusive, and comprising siloxane units chosen from the group formed by the following units: $(CH_3)_3SiO_{1/2}$, $(CH_3)_2SiO_{2/2}$, $CH_3SiO_{3/2}$ and $SiO_{4/2}$.

The volatile fluid methylsiloxane preferably comprises essentially dimethylsiloxane units and optionally trimethylsiloxane units. Volatile dimethicones that are more particularly preferred are cyclic siloxanes of general formula $[(CH_3)_2SiO]_x$ and linear siloxanes of general formula $(CH_3)_3SiO[(CH_3)_2SiO]_ySi(CH_3)_3$, and their mixtures, in the formula of which x denotes an integer ranging from 3 to 6 and y denotes an integer ranging from 0 to 4.

The linear volatile dimethicones generally exhibit viscosities of less than approximately 5 centistokes at 25° C. whereas those of the cyclic volatile dimethicones are less than approximately 10 centistokes at 25° C.

Examples of such preferred dimethicones include, for example (non-limiting list): SILBIONE 70 045 V2 oil, sold by the company Rhône-Poulenc, and DC 244 FLUID, sold by the company Dow Corning, which are cyclotetradimethylsiloxanes, DC 245 FLUID, sold by the company Dow Corning, which is a cyclopentadimethylsiloxane, and BELSIL DM 0 65, sold by the company Wacker, which is a hexamethyldisiloxane.

The volatile dimethicone is preferably present in the water-in-silicone emulsion according to the invention in proportions by weight ranging from approximately 1 to approximately 25%, preferably from approximately 1 to approximately 15%, with respect to the whole of the emulsion, (b) the silicone emulsifying agent is preferably chosen from the group formed by the polydiorganosiloxanes of following formulae (I) and (II), it being possible for these compounds themselves to be dispersed in a volatile dimethicone,

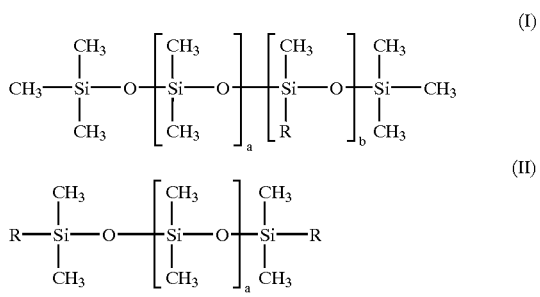

in which,

R is independently the group: —$C_nH_{2n}$—(—$OC_2H_4$—)$_x$—(—$OC_3H_6$—)$_y$—O—R', R' denotes a hydrogen atom or a linear or branched alkyl radical containing from 1 to approximately 12 carbon atoms, a and b independently denote an integer ranging from 1 to approximately 500, n is an integer ranging from 2 to 12, x and y independently denote an integer ranging from 0 to approximately 50, the sum x+y being greater than or equal to the value 1.

The emulsifying polydiorganosiloxane is preferably a polymer of formula (I) in which a is an integer ranging from 2 to 450, b is an integer ranging from 2 to 40, n is an integer ranging from 2 to 5, x is an integer ranging from 1 to 30 and y is an integer ranging from 0 to 30, with x≧y.

Advantageously, according to the invention, the emulsifying polydiorganosiloxane is provided as a dispersion in a volatile dimethicone, the dispersion preferably comprising, for example by volume, from 1 to 20% of polydiorganosiloxane and from 80 to 99% of volatile dimethicone. A particularly preferred dispersion comprises, by volume, 10% of polydiorganosiloxane in the volatile dimethicone. Thus, a more particularly preferred silicone emulsifier according to the invention is a mixture of cyclomethicone and of dimethicone copolyol (C.T.F.A. nomenclatures, 4th edition, 1991) sold by the company Dow Corning under the trade name SILICONE DC 3225 C.

In the preferred water-in-silicone emulsions according to the invention, the emulsifying polydiorganosiloxane of formula (I) or (II) is generally present in proportions by weight ranging from approximately 0.1% to approximately 20%, preferably from approximately 0.5% to approximately 15%, and the aqueous phase represents an amount by weight ranging from approximately 15% to approximately 90%, and the continuous silicone fatty phase represents from approximately 10% to approximately 85% of the total weight of the emulsion.

Transparent emulsions of this type can be obtained when the refractive index (ri) of the aqueous phase is in the region of the refractive index of the continuous silicone fatty phase: Δri=(ri of the silicone fatty phase–ri of the aqueous phase) <0.01.

When the deodorant compositions according to the invention are intended for cosmetic use, they can be provided in the form of lotions, creams or fluid gels, distributed as an aerosol spray, as a pump-action spray or as a roll-on, in the form of thick creams distributed in tubes and in the form of sticks, and can contain, in this respect, the ingredients and propellants generally used in this type of product and that are well known to the person skilled in the art, with the proviso that they do not interfere with the water-soluble zinc salt described in the present invention.

The invention can also find advantageous applications in the field of various deodorizing and cleansing products (surrounding air, textiles, refrigerators, rubbish chutes, dustbins, domestic animal cages and litter or building ventilation shafts).

Concrete, but in no way limiting, examples illustrating the invention will now be given.

EXAMPLES

Example 1

An odour absorption test was carried out with respect to natural sweat.

It was ensured beforehand that this test was truly an odour absorption test by confirming that a sample containing a bactericide, such as triclosan, had no absorption effect on the smell of sweat.

The axillary sweat from a number of people was thus removed in a sauna and combined to produce a sweat sample. In order to obtain the characteristic nauseating smell of sweat, before introducing the active substance, this sweat sample was incubated for 14 hours at a temperature of 37° C. 1 ml of the incubated sweat sample was introduced into each flask of active substance to be tested and into a control flask (without active substance). The active substance: 5.5 mg of Zn ion in the form of zinc pidolate, zinc chloride, zinc gluconate, zinc lactate, zinc phenolsulphonate and zinc sulphate, was then introduced respectively into each of the flasks of active substance to be tested.

The flasks were then incubated for a second time for 24 hours at a temperature of 37° C. and then for a third time for 3 days at room temperature.

Eight judges then smelled ("sniff test") each of these flasks and graded the intensity of the smell on a scale from 0 to 4.

Grade 0=no smell

Grade 4=strong smell.

Results: The control flask, without water-soluble zinc salt, was graded 4, whereas the flasks containing the water-soluble zinc salts mentioned above were graded from 1.25 to 1.68, the best results having been obtained with zinc pidolate.

These results demonstrate that water-soluble zinc salts exhibit a significant absorption capacity for the smells from natural sweat.

Example 2

The two following formulae were prepared (an aqueous lotion and a water-in-silicone emulsion):
Aqueous Lotion:
Zinc pidolate . . . 3 g
Demineralized water . . . q.s. for 100 g
Water-in-Silicone-Emulsion:
　A/ Fatty phase:
　　SILBIONE 70 045 V2 oil . . . 6.6 g
　　Silicone DC 3225 C . . . 9.4 g
　B/ Aqueous phase:
　　Zinc pidolate . . . 3 g
　　Ethyl alcohol . . . 11.1 g
　　Propylene glycol . . . 38.7 g
　　Demineralized water . . . q.s. for 100 g
The phase B was slowly poured into the phase A, with gentle mechanical stirring and at room temperature. The mixture was then further stirred for 5 minutes while gradually increasing the stirring rate.

The deodorizing effectiveness (by absorption of the smell from natural sweat) of these two formulae, each containing the same amount of zinc pidolate, was then measured in vivo.

The aqueous lotion, on the one hand, and the emulsion, on the other hand, which are described above, were applied under one armpit, the other armpit serving as control, on 20 people who had been conditioned beforehand (that is to say, not having received the application of a bactericidal deodorant or of an antiperspirant deodorant for one week).

Ten judges then carried out the "sniff test" and graded the intensity of the smell according to a scale from 0 to 9.

Grade 0=no smell

Grade 9=extremely powerful smell.

The results, expressed by the [mean of the grades of the control armpits]–[means of the grades of the treated armpits] difference, were as follows:

aqueous lotion=0.5 water-in-silicone emulsion=1.1.

These results demonstrate that the formula as an emulsion has a deodorizing effectiveness by absorption of the smells from natural sweat that is greater than that of the aqueous lotion.

Example 3

A transparent deodorant gel of the following composition was prepared:
Water-in-Silicone Emulsion:
　A/ Fatty phase:
　　Silicone DC 244 Fluid . . . 6.5 g
　　Silicone DC 3225 C . . . 9.4 g
　B/ Aqueous phase:
　　Zinc sulphate ($ZnSO_4.7H_2O$) . . . 4.1 g
　　Glycerol . . . 37 g
　　Demineralized water . . . q.s. for 100 g
This cosmetic gel was effective in absorbing human axillary smells.

We claim:

1. A deodorant composition in the form of a water-in-silicone emulsion, comprising at least one water-soluble zinc salt in an amount effective to absorb odor and further comprising water in an amount sufficient to form said emulsion.

2. A composition according to claim 1, wherein said at least one water-soluble zinc salt is a zinc salt of an organic or inorganic acid having a solubility of at least 0.3% by weight, expressed as Zn ion.

3. A composition according to claim 1, wherein said at least one water-soluble zinc salt is a zinc pyrrolidonecarboxylate.

4. A composition according to claim 1, wherein said at least one water-soluble zinc salt is selected from zinc sulphate, zinc chloride, zinc lactate, zinc gluconate and zinc phenolsulphonate.

5. A composition according to claim 1, wherein said at least one water-soluble zinc salt is present in a concentration by weight as Zn ion ranging from 0.01 to 10% with respect to the total weight of the composition.

6. A composition according to claim 5, wherein said at least one water-soluble zinc salt is present in a concentration by weight as Zn ion ranging from 0.1 to 5% with respect to the total weight of the composition.

7. A composition according to claim 6, wherein said at least one water-soluble zinc salt is present in a concentration by weight as Zn ion ranging from 0.1 to 2%.

8. A method of preparing a cosmetic product intended for human topical application, comprising the step of including in said product a composition as defined in claim 1.

9. A method according to claim 8, wherein said product is a deodorant.

10. A method for treating human axillary smells, comprising the step of applying an effective amount of a composition as defined in claim 1 on the human axillary surface.

11. A composition according to claim 1, wherein said water-soluble zinc salt is the sole odor absorbing agent in said composition.

* * * * *